US011239701B2

(12) United States Patent
Petersen (10) Patent No.: US 11,239,701 B2
(45) Date of Patent: *Feb. 1, 2022

(54) RESONANT POWER TRANSFER SYSTEMS HAVING EFFICIENCY OPTIMIZATION BASED ON RECEIVER IMPEDANCE

(71) Applicant: TC1 LLC, St. Paul, MN (US)

(72) Inventor: Ethan Falk Petersen, Oakland, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/024,454

(22) Filed: Sep. 17, 2020

(65) Prior Publication Data
US 2021/0135497 A1 May 6, 2021

Related U.S. Application Data

(63) Continuation of application No. 16/197,562, filed on Nov. 21, 2018, now Pat. No. 10,804,744, which is a
(Continued)

(51) Int. Cl.
*H02J 50/12* (2016.01)
*A61M 60/871* (2021.01)
(Continued)

(52) U.S. Cl.
CPC ........... *H02J 50/12* (2016.02); *A61M 60/871* (2021.01); *H02J 7/025* (2013.01); *A61M 60/873* (2021.01);
(Continued)

(58) Field of Classification Search
CPC ........... H04B 5/0037; B60L 53/12–126; B60L 53/34; B60L 53/38–39; H01F 38/14;
(Continued)

(56) References Cited

U.S. PATENT DOCUMENTS

| | | | |
|---|---|---|---|
| 7,504,905 B1* | 3/2009 | Steinbrecher | H02J 50/10 333/24 C |
| 2010/0066176 A1* | 3/2010 | Azancot | H02J 50/12 307/104 |

(Continued)

OTHER PUBLICATIONS

"Thevenin's theorem", Aug. 3, 2015, Wikipedia, retrieved via Wayback Machine at <https://web.archive.org/web/20150803171519/ https://en.wikipedia.org/wiki/Th%C3%A9venin's_theorem> (Year: 2015).*

*Primary Examiner* — Hal Kaplan
*Assistant Examiner* — David A Shiao
(74) *Attorney, Agent, or Firm* — Armstrong Teasdale LLP (57) ABSTRACT

The present disclosure provides systems and methods for controlling wireless power transfer systems. A wireless power transfer system includes a transmitter driven by a power source and a transmit controller, wherein the transmitter is configured to control delivery of wireless power, and a receiver inductively coupled to the transmitter, the receiver configured to receive the wireless power from the transmitter and deliver the received wireless power to a load. The receiver includes receiver electronics configured to determine a Thevenin equivalent impedance of the wireless power transfer system, determine a Thevenin equivalent source voltage of the wireless power transfer system, and control, based on the determined Thevenin equivalent impedance and the determined Thevenin equivalent source voltage, an ideal source voltage of the receiver to vary the amount of the wireless power transferred from the transmitter to the receiver.

18 Claims, 9 Drawing Sheets

Related U.S. Application Data continuation of application No. 15/286,930, filed on Oct. 6, 2016, now Pat. No. 10,177,604.

(60) Provisional application No. 62/238,586, filed on Oct. 7, 2015.

(51) Int. Cl.
*H02J 7/02* (2016.01)
*A61M 60/873* (2021.01)
*H02J 50/80* (2016.01)

(52) U.S. Cl.
CPC ...... *A61M 2205/8243* (2013.01); *H02J 50/80* (2016.02)

(58) Field of Classification Search
CPC ............. A61B 1/00029; A61N 1/3787; A61M 2205/8243; A61M 60/873–875
See application file for complete search history.

(56) References Cited

U.S. PATENT DOCUMENTS

| | | | | |
|---|---|---|---|---|
| 2012/0155136 | A1* | 6/2012 | Von Novak | H02J 50/12 363/126 |
| 2014/0042821 | A1* | 2/2014 | Boys | H01F 38/14 307/104 |
| 2014/0092649 | A1* | 4/2014 | Hsu | H02M 5/42 363/34 |
| 2014/0320090 | A1* | 10/2014 | Keeling | B60L 53/12 320/162 |
| 2015/0202970 | A1* | 7/2015 | Huang | H02J 50/40 320/108 |
| 2015/0249345 | A1* | 9/2015 | Kashiwagi | H02J 50/12 307/104 |
| 2015/0290373 | A1* | 10/2015 | Rudser | A61M 60/871 623/3.27 |
| 2015/0357991 | A1* | 12/2015 | Ono | H02J 7/00034 320/108 |

* cited by examiner

RESONANT POWER TRANSFER SYSTEMS HAVING EFFICIENCY OPTIMIZATION BASED ON RECEIVER IMPEDANCE

CROSS REFERENCE TO RELATED APPLICATIONS

This application is continuation of U.S. application Ser. No. 16/197,562, filed on Nov. 21, 2018, which is a continuation of U.S. application Ser. No. 15/286,930, filed on Oct. 6, 2016, which claims priority to U.S. Provisional Patent Application No. 62/238,586, filed Oct. 7, 2015, all of which are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to resonant wireless power transfer systems, and more specifically to communication systems and methods for implantable resonant wireless power transfer systems.

BACKGROUND

Many types of devices require transmitting energy between locations. Recent advances have accelerated the pace of innovation for wireless energy transmission (WET) without the use of cords. An example of a system using wireless energy technology is a powered, implantable medical device.

Many implantable medical devices require electrical systems to power the implant. Typically, this is achieved using percutaneous wiring to connect a power source to the implant. More recently, there has been interest in development of Transcutaneous Energy Transfer (TET) systems, e.g., through an oscillating magnetic field, for powering implantable medical devices.

A TET system usually includes a number of components or systems. A conventional TET system is implemented with a transmitting coil and a receiving coil for transmitting energy across the skin layer. The system typically includes a controller for driving the transmitting coil and/or controlling the implanted electronics.

Typically, implantable medical devices, such as implanted sensors, require very little power to operate. With such low power levels (on the order of milliwatts), power transfer levels and efficiency can be lower. With higher power devices (e.g., on the order of watts and up to 15 W or more), efficient transfer of wireless power is extremely important. Additionally, positions within the body are limited that can accommodate larger implanted devices, some of which are deep below the skin surface. These implant locations require additional attention to position and orientation of both the transmit and receive coils, as well as techniques to improve and maximize transfer efficiency.

Previous TET systems for implantable medical devices required the implanted receiver coil to be positioned just under the skin, and typically include a mechanical feature to align the receive and transmit coils and keep them together. By implanting these devices directly under the skin, the size and power requirements of these implanted devices is limited if they are to be powered by a TET system. TET systems can be designed for operation even while power is not being received by the receiver coil. In a typical configuration, solid-state electronics and a battery can power the implanted medical device when external power is interrupted or not available.

For higher power devices, efficiency and heat losses become very important. Heat loss in an implanted device is limited by the acceptable temperature rise of the surrounding tissue. Typically a 2° C. temperature rise in tissue is the acceptable limit before risking thermal damage to the surrounding tissue. This is a relatively small temperature rise, meaning the acceptable heat loss in an implant is also small. As a result, the power efficiency of a TET system is very important.

BRIEF DESCRIPTION

In one embodiment, the present disclosure is directed to a wireless power transfer system. The wireless power transfer system includes a transmitter driven by a power source and a transmit controller, wherein the transmitter is configured to control delivery of wireless power, and a receiver inductively coupled to the transmitter, the receiver configured to receive the wireless power from the transmitter and deliver the received wireless power to a load. The receiver includes receiver electronics configured to determine a Thevenin equivalent impedance of the wireless power transfer system, determine a Thevenin equivalent source voltage of the wireless power transfer system, and control, based on the determined Thevenin equivalent impedance and the determined Thevenin equivalent source voltage, an ideal source voltage of the receiver to vary the amount of the wireless power transferred from the transmitter to the receiver.

In another embodiment, the present disclosure is directed to a receiver for use in a wireless power transfer system. The receiver is configured to receive wireless power from a transmitter driven by a power source and a transmit controller, and configured to deliver the received wireless power to a load. The receiver includes a receiving coil, and receiver electronics coupled to the receiving coil. The receiver electronics are configured to determine a Thevenin equivalent impedance of the wireless power transfer system, determine a Thevenin equivalent source voltage of the wireless power transfer system, and control, based on the determined Thevenin equivalent impedance and the determined Thevenin equivalent source voltage, an ideal source voltage of the receiver to vary the amount of the wireless power transferred from the transmitter to the receiver.

In yet another embodiment, the present disclosure is directed to a method for controlling a wireless power transfer system. The wireless power transfer system includes a receiver inductively coupled to a transmitter, the receiver configured to receive wireless power from the transmitter and deliver the received wireless power to a load. The method includes determining, using receiver electronics at the receiver, a Thevenin equivalent impedance of the wireless power transfer system, determining, using the receiver electronics, a Thevenin equivalent source voltage of the wireless power transfer system, and controlling, using the receiver electronics, based on the determined Thevenin equivalent impedance and the determined Thevenin equivalent source voltage, an ideal source voltage of the receiver to vary the amount of the wireless power transferred from the transmitter to the receiver.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the disclosure are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/0027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter. In some cases, "loosely coupled" or "loose coupling" refers a highly resonant system and/or a system using strongly-coupled magnetic resonators.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. Examples of closely coupled system with resonant coils are described in International Pub. Nos. WO2001/037926; WO2012/087807; WO2012/087811; WO2012/087816; WO2012/087819; WO2010/030378; and WO2012/056365, U.S. Pub. No. 2003/0171792, and U.S. Pat. No. 5,350,413 (now abandoned), incorporated herein for all purposes by reference.

For given coil sizes and separations, coupling a given amount of power requires generating the same magnetic field strength for either inductive or resonant systems. This requires the same number of ampere-turns in the coils. In inductive systems, all the ampere-turns pass through the MOSFETs and generate power losses in their on-state resistance. In resonant systems, only the exciter ampere-turns pass through the MOSFETs, while the resonator ampere-turns do not. As a consequence, resonant systems will always have lower losses and higher efficiencies than inductive systems of the same dimensions and power through-put.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Figure 1:
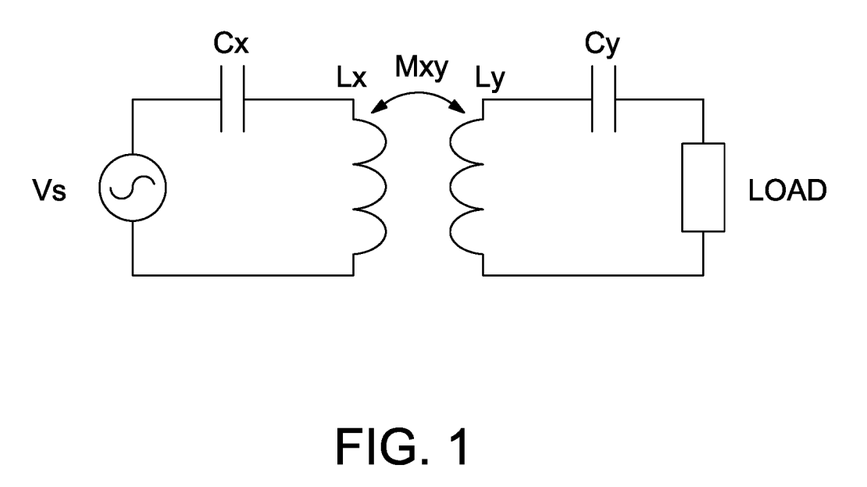
FIG. 1 illustrates a basic wireless power transfer system.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \mu J \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74\text{A peak}$$

$$v_y = \omega L_y i_y = 352\text{V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \mu J}{0.05} = 8.4 mJ$$

For the same circuit the self inductance of the transmitter coil was 146 uH as mentioned above. This results in:

$$i_x = \sqrt{\frac{2e_x}{L}} = 10.7\text{A peak}$$

$$v_x = \omega L_x i_x = 2460\text{V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
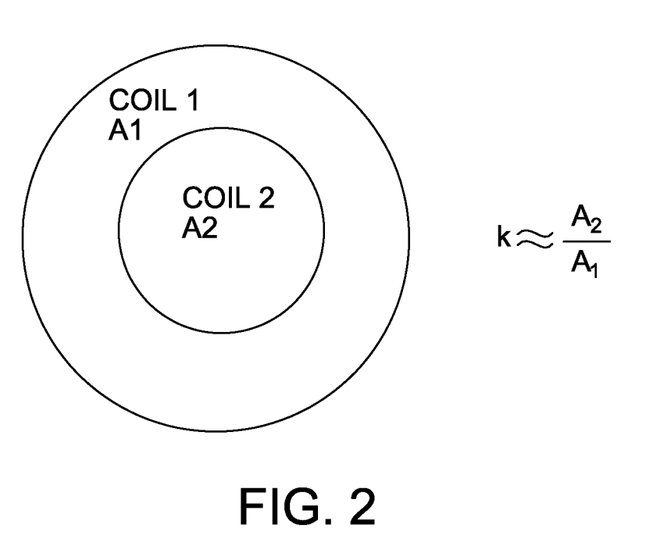
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
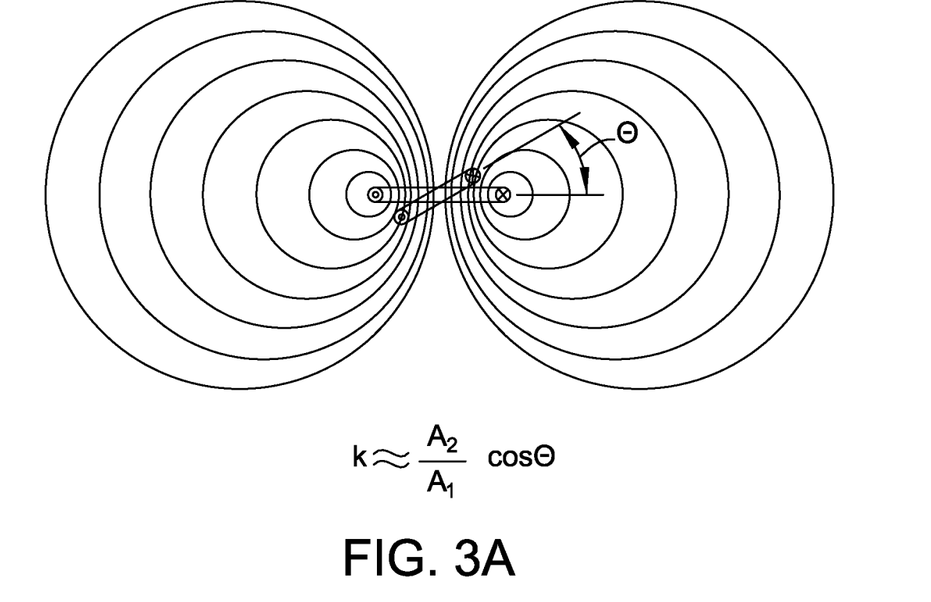
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
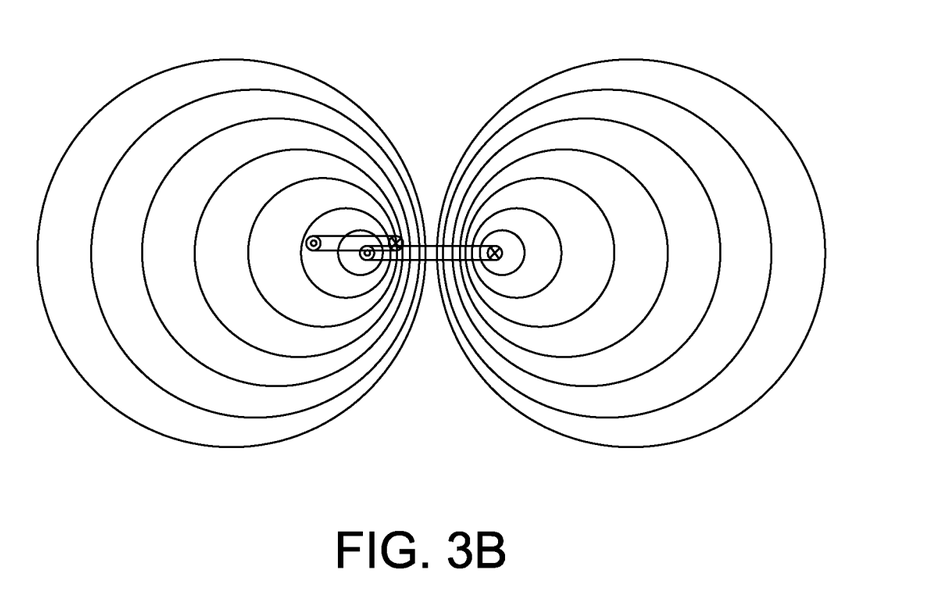

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

Figure 4:
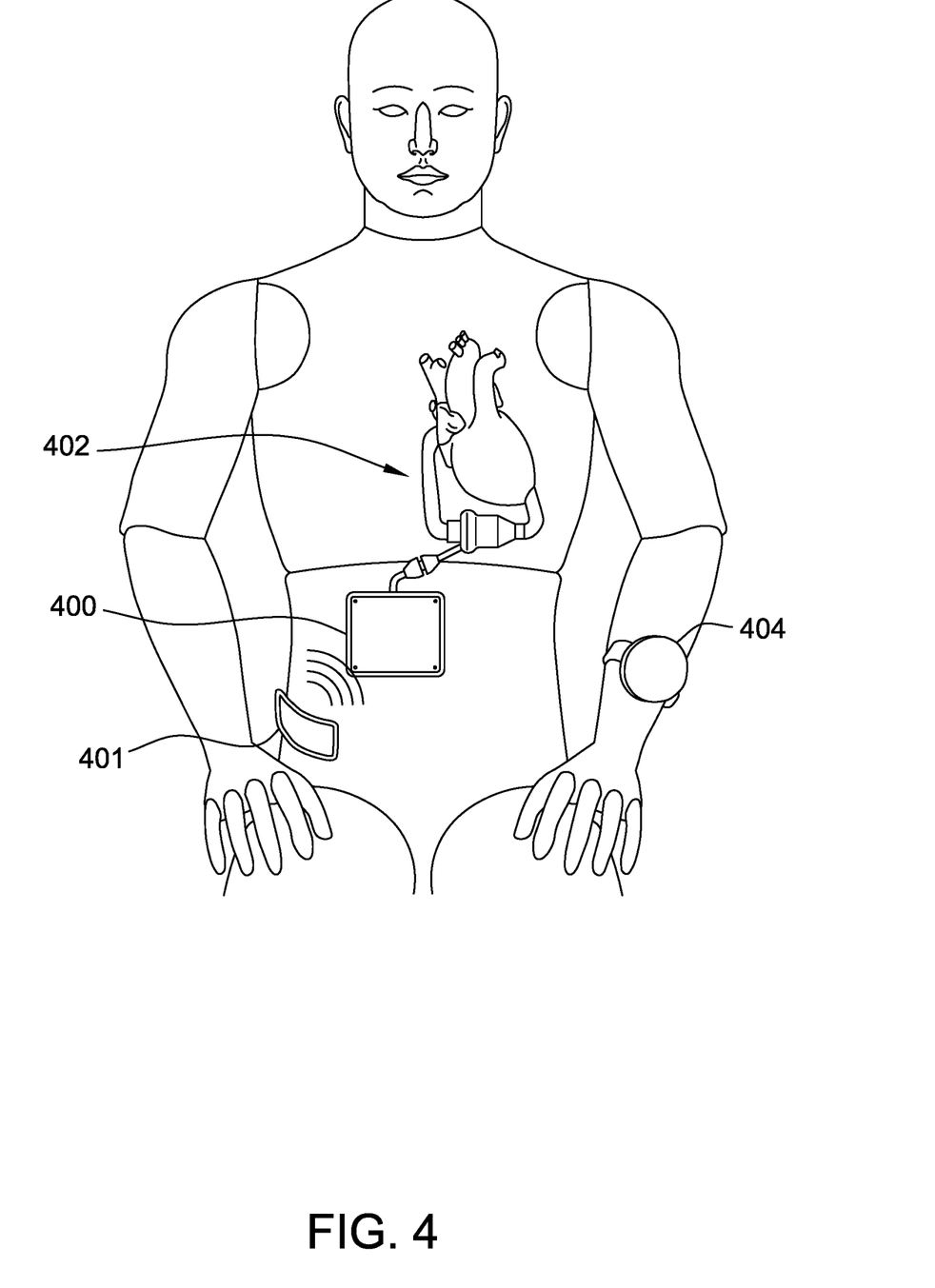
FIG. 4 illustrates a wireless power transfer system comprising an implantable TETS receiver unit implanted in an abdomen of a human patient.

FIG. 4 illustrates a wireless power transfer system comprising an implantable TETS receiver unit 400 implanted in an abdomen of a human patient. The receiver unit 400 can be coupled to a device load 402, such as an implantable medical device, e.g., an implantable LVAD or heart pump. The exemplary receiver unit 400 can include a receiver resonator coil and electronics configured to receive wireless energy from an external transmitter 401, which can include a power supply such as a pulse generator connected to a transmitter resonator coil. In one embodiment, the electronics and coils are implanted separately and connected by an implanted cable. In some embodiments, external controller 404 can be configured to communicate with the TETS receiver unit 400 and can be worn by the patient, such as on the patient's wrist. In other embodiments, the external controller can be an electronic computing device such as a personal computer, a tablet, smartphone, or laptop computer.

In some embodiments, the receiver unit 400 further includes communications electronics configured to send and receive communications data to and from other electronic devices inside and outside of the body. In one embodiment, the receiver unit further includes an internal rechargeable power source. In various embodiments, the receiver unit 400 of the TET system is configured as a single implanted device including the receive coil, antenna, power source, and associated circuitry. The receiver unit is configured so the implantable medical device can be plugged directly into the unit. The single housing configuration makes implantation easier and faster. Additionally, since there are less implants, and consequently less tunneling in the body and percutaneous defect sites, adverse event risks like bleeding and infection are reduced. One of skill will appreciate from the description herein that various internal components of the system can be bundled together or implanted separately. For example, the internal rechargeable power source can be implanted separately from the receiver unit and connected by a power cable. The antenna assembly, power source, and receive coil can all be configured in separate hermetically sealed housings. International Pub. No. WO2007/053881A1, U.S. Pub. No. 2014/0005466, and U.S. Pat. No. 8,562,508, the entire contents of which are incorporated herein for all purposes by reference, disclose several exemplary configurations.

TET systems of the present disclosure provide solutions for optimizing efficiency to maximize battery life and to minimize heat in both the implanted receiver and the external transmitter. The most efficient operating condition is where the current in the resonant system is as small as possible. However, if the current is too small, the TET system will not be able to transfer enough power. If the TET system tries to pull more power out of the resonators than can be supported, the resonant system collapses which results in no power transfer.

According to the present disclosure, the receiver unit can be configured to monitor the impedance of the transmit and receive resonators and calculate the amount of power than can be transferred through the TET system. The receiver unit can use this calculated amount of power to limit how much power the receiver unit pulls out of the resonant system and avoid collapse of the system. If the receiver unit requires more power than it is pulling from the resonant system, the receiver unit can communicate the need for more power to the transmitter unit (e.g., by transmitting a control message from the receiver to the transmitter), which can then drive the resonators with more current to transfer additional power. This allows the TET system to run at the minimum amount of current required to transfer the desired amount of power, which minimizes losses in the system.

The receiver can communicate with the transmitter using any suitable communications techniques. For example, TETs power signals between the transmitter and receiver may be modulated to communicate information between the transmitter and receiver. Alternatively, a separate radio may be used to send messages from the receiver to the transmitter. Further, optical or acoustic communication methods may be used as well. U.S. Pub. No. 2015/0222139, which is incorporated by reference herein in its entirety, discussion communications between a receiver and a transmitter in a wireless energy transfer system.

Figure 5:
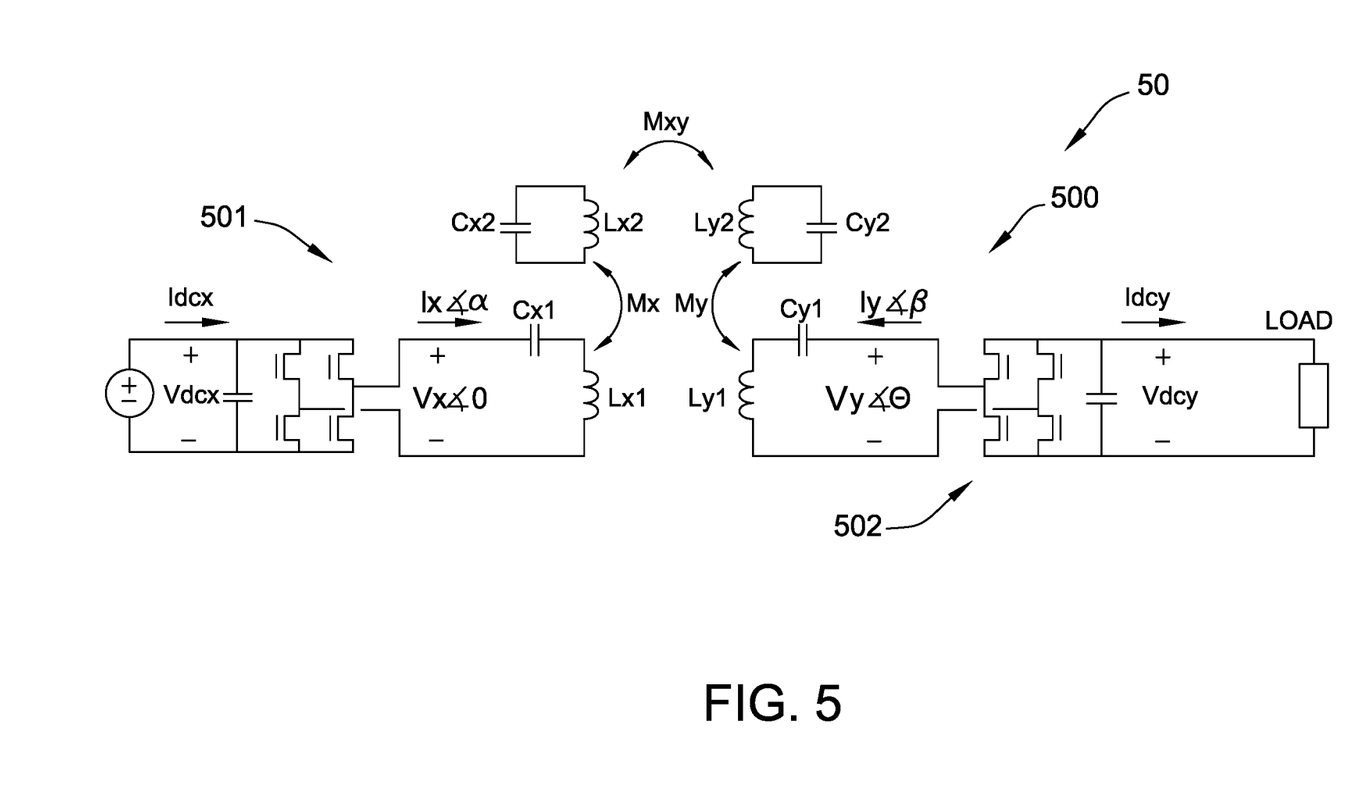
FIG. 5 illustrates one embodiment of a TET system 5, including a receiver and a transmitter.

FIG. 5 illustrates one embodiment of a TET system 50, including a receiver 500 and a transmitter 501. The circuit shown in FIG. 5 can further modeled as a two port network, shown in FIG. 6. The transmitter power electronics are modeled as an ideal voltage source, Vx. The receiver power electronics are also modeled as an ideal voltage source, Vy. The currents and voltages are described using a phasor notation.

Figure 6:
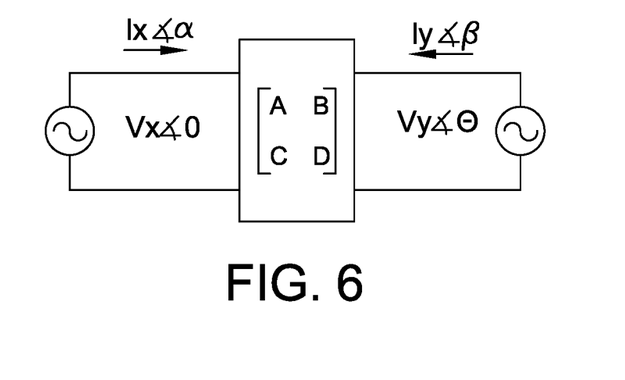
FIG. 6 illustrates the circuit of FIG. 5 modeled as a two port network.
Figure 7:
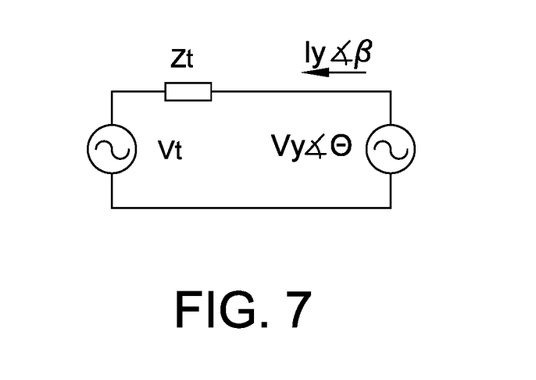
FIG. 7 shows the two port network of FIG. 6 modeled as a Thevenin equivalent circuit.

From the point of view of the receiver, the two port network of FIG. 6 can be represented by the Thevenin equivalent circuit. The resonant system appears to be a voltage source and an impedance, as shown in FIG. 7. The impedance Zt is a function of the resonant system's inductance and capacitance, so it changes as the mutual coupling between the transmitter and the receiver changes. The relative position of the transmitter and receiver changes the impedance Zt. The voltage source Vt changes both magnitude and phase as a function of the mutual coupling, and the transmitter voltage Vx.

Figure 8:
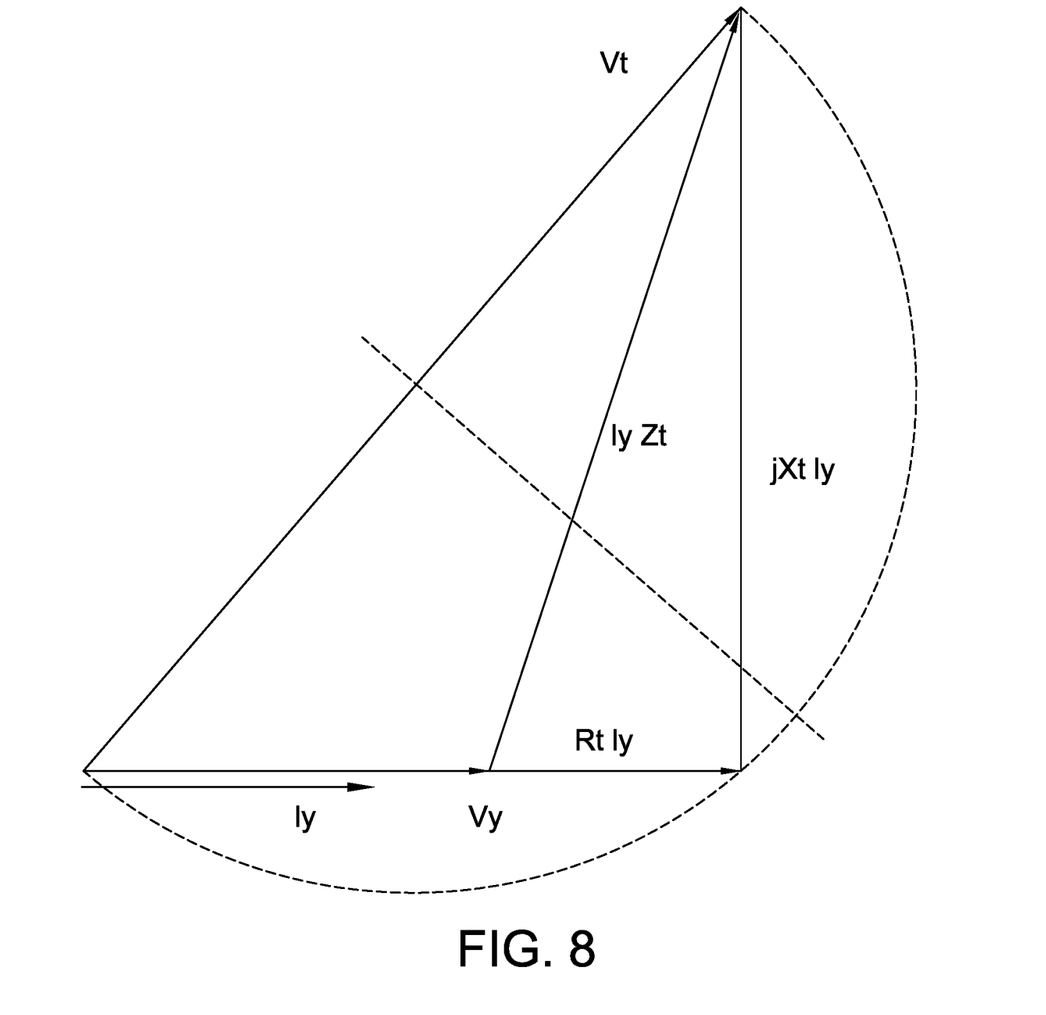
FIG. 8 shows operation of the circuit of FIG. 5 as illustrated by a phasor diagram.

The receiver electronics are able to control the voltage source, Vy, to get a specific voltage magnitude and phase. The operation of the circuit is illustrated by the phasor diagram in FIG. 8. This diagram shows the voltage source Vy is controlled to be in phase with the current Iy. The TET system is configured to transfer the maximum amount of power when the magnitude of Vy is equal to the magnitude of IyZt. To control the power through the resonators, the circuit can be controlled in a couple ways, including:

Method 1: For many systems the magnitude of Vt and Zt are large. There is a limit to the magnitude of Vy. In the system shown in FIG. 5, the limit is the DC bus voltage of the receiver. If Vt is large relative to Vy, the power through the system can be controlled by adjusting the magnitude of Vy. Increasing Vy increases the amount of power through the system.

Method 2: In another embodiment, the way to control the amount of power only works if the magnitude of Vt is smaller than the largest possible magnitude of Vy. If Vy is equal to Vt then no power is transferred through the system. As Vy is reduced then the amount of power absorbed by the receiver increases.

To avoid having the receiver try to pull more power than the system can handle, it is possible to limit the magnitude of the voltage Vy, to be always less than IyZt for control method 1, or always greater than IyZt. This way the resonance never collapses. If Zt and Iy are known it is possible to know how close to the power limit the system is operating. If the system is operating too close to the limit, the receiver can communicate this information to the transmitter, which can turn up its output, Vx, effectively turning up Vt, so the system can transfer more power. For example, in some embodiments, if a difference between IyZt and Vy is less than a predetermined threshold, the receiver transmits a control message to the transmitter to cause the transmitter to increase Vx. In this way, the transmitter output can be optimized to run at the minimum current needed, minimizing losses, achieving the most efficient operation possible.

To measure Zt it is possible for the receiver to vary the voltage Vy and observe the change in Iy. Specifically, if Vy is varied by a predetermined amount (referred to as 'dither'), in a sampled data system, we have:

$$Vy[n]=Vy[n-1]\pm\text{dither}$$

Further, the Thevenin equivalent impedance is then:

$$Zt[n] = \frac{Vy[n] - Vy[n-1]}{Iy[n] - Iy[n-1]}$$

The values in these equations are phasors. Accordingly, the mathematical operations are performed using complex numbers. This method of calculating Zt works if the voltage Vt is constant and the value of Zt is constant. This will be true if the voltage Vx is constant and the transmitter and receiver are not moving relative to one another. In practice, it can be assumed that any relative movement of the transmitter and receiver is very slow compared to the voltage signal Vy. Further, in practice, Vx is controlled, so it does change. However, as long as the control system driving Vx is slow as compared to the voltage signal Vy, and any relative movement of the transmitter and receiver is relatively slow, the measured result of Zt is close enough to the actual value to facilitate optimizing power transfer.

Figure 9:
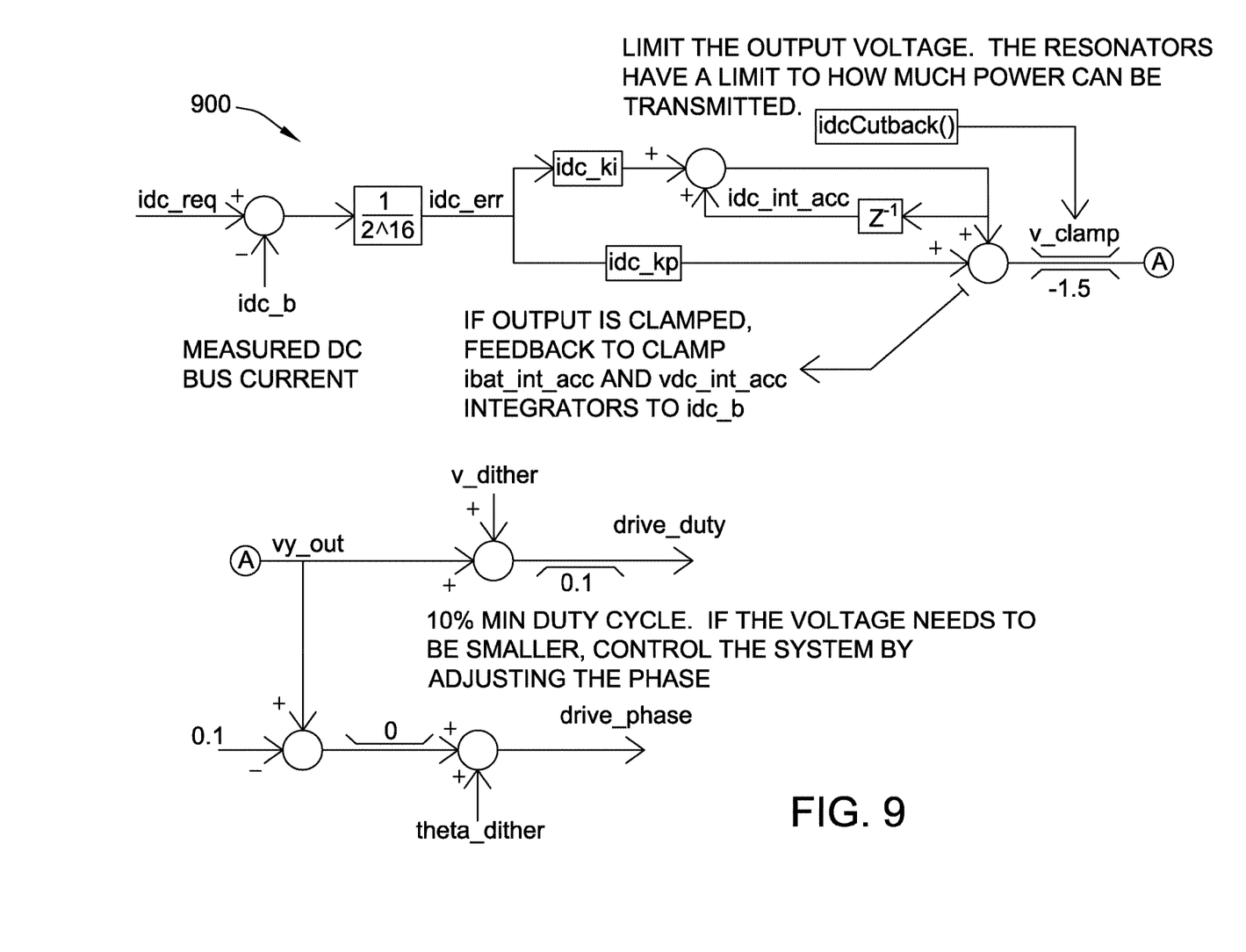
FIG. 9 shows a diagram of a control system for a receiver according to one embodiment of the present disclosure.

FIG. 9 shows a diagram of one embodiment of a control system 900 for a receiver according to one embodiment of the present disclosure. In this embodiment, control system 900 is implemented using the receiver electronics. Control system 900 adjusts the magnitude and phase of the voltage signal Vy in order to achieve a desired current Idcy (shown in FIG. 5). Control system 900 is used when IyZt is larger than Vy, so that increasing Vy results in an increase in power received by the receiver.

In this embodiment, the voltage Vy is driven by a MOSFET bridge 502 (shown in FIG. 5) that connects the Vdcy and Vy circuits. MOSFET bridge 502 is controlled by a pulse width modulated signal from a microcontroller (e.g., as part of the receiver electronics). Specifically, control system 900 controls a duty cycle and phase of the pulse width modulated signal, resulting in Vy. The phase is controlled such that Vy is almost always in phase with Iy. The exception occurs when the desired voltage is very small (at which point the duty cycle is clamped at a minimum value and control system 900 adjusts the phase of the output voltage).

In this embodiment, control system 900 adjusts Vy in order to achieve a described Idcy value. The amount of desired current is based on the demands of the receiver. In this embodiment, control system 900 is implemented using a proportional integrative (PI) controller. Alternatively, control system 900 may be implemented using any suitable controller. The output of the PI controller is limited by v_clamp, as shown in FIG. 9. v_clamp is the maximum allowed voltage and is calculated by a function called IdcCutback. This function observers the resonator impedance (Zt) and calculates IyZt. In this embodiment, the magnitude of IyZt is the maximum voltage possible for Vy, and IyZt is used for v_clamp. This facilitates limiting the power the receiver can pull from the resonant system to prevent the resonance from collapsing.

Figure 10:
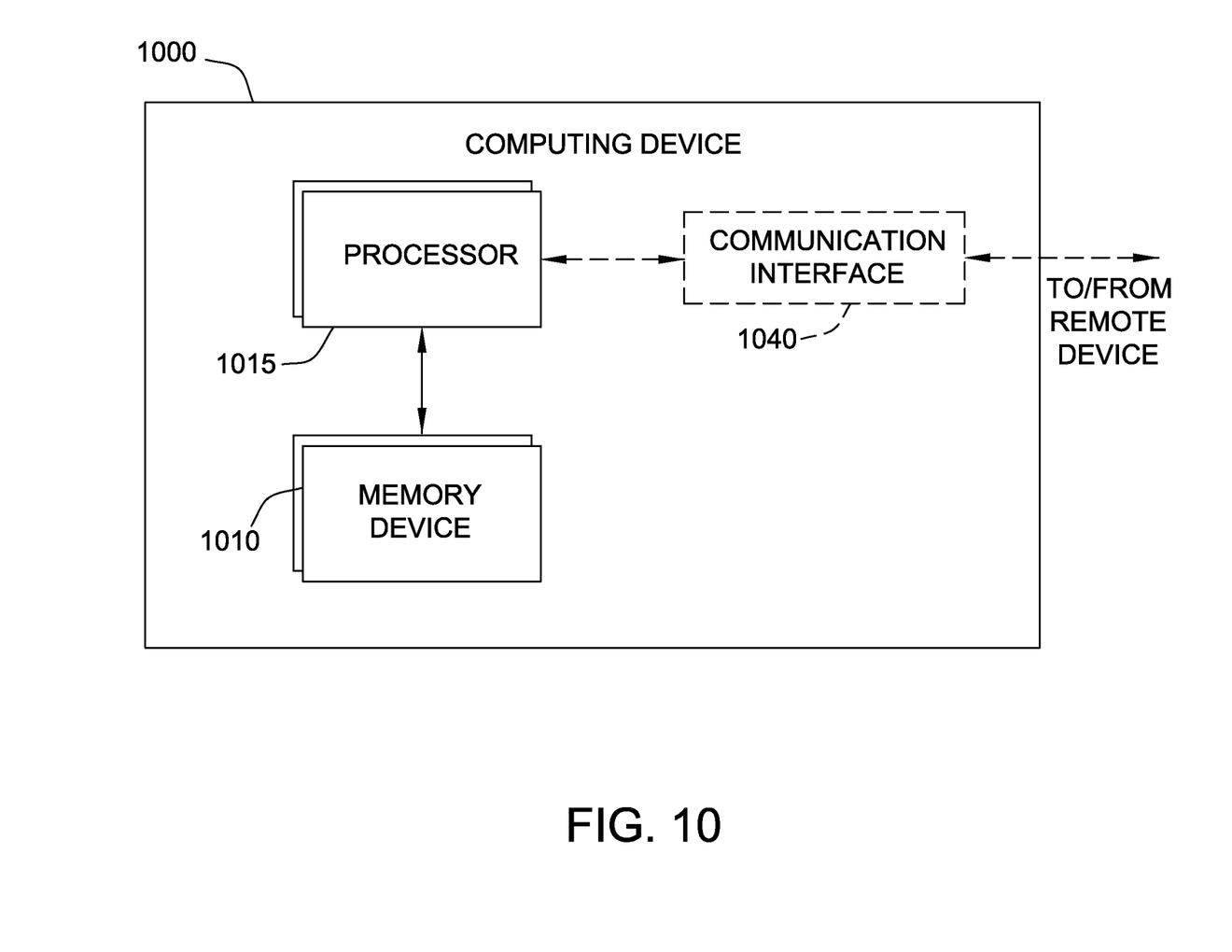
FIG. 10 is a block diagram of one embodiment of a computing device that may be used to implement receiver electronics.

In some embodiments, the receiver electronics are implemented as a computing device. For example, FIG. 10 is a block diagram of one embodiment of a computing device 1000 that may be used to perform the functions of the receiver electronics.

In this embodiment, computing device 1000 includes at least one memory device 1010 and a processor 1015 that is coupled to memory device 1010 for executing instructions. In some embodiments, executable instructions are stored in memory device 1010. In the illustrated embodiment, computing device 1000 performs one or more operations described herein by programming processor 1015. For example, processor 1015 may be programmed by encoding an operation as one or more executable instructions and by providing the executable instructions in memory device 1010.

Processor 1015 may include one or more processing units (e.g., in a multi-core configuration). Further, processor 1015 may be implemented using one or more heterogeneous processor systems in which a main processor is present with secondary processors on a single chip. In another illustrative example, processor 1015 may be a symmetric multi-processor system containing multiple processors of the same type. Further, processor 1015 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 1010 is one or more devices that enable information such as executable instructions and/or other data to be stored and retrieved. Memory device 1010 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 1010 may be configured to store, without limitation, application source code, application object code, source code portions of interest, object code portions of interest, configuration data, execution events and/or any other type of data.

Computing device 1000, in the illustrated embodiment, includes a communication interface 1040 coupled to processor 1015. Communication interface 240 communicates with one or more remote devices, such as the transmitter. To communicate with remote devices, communication interface 140 may include, for example, a wired network adapter, a wireless network adapter, a radio-frequency (RF) adapter, and/or a mobile telecommunications adapter.

Figure 11:
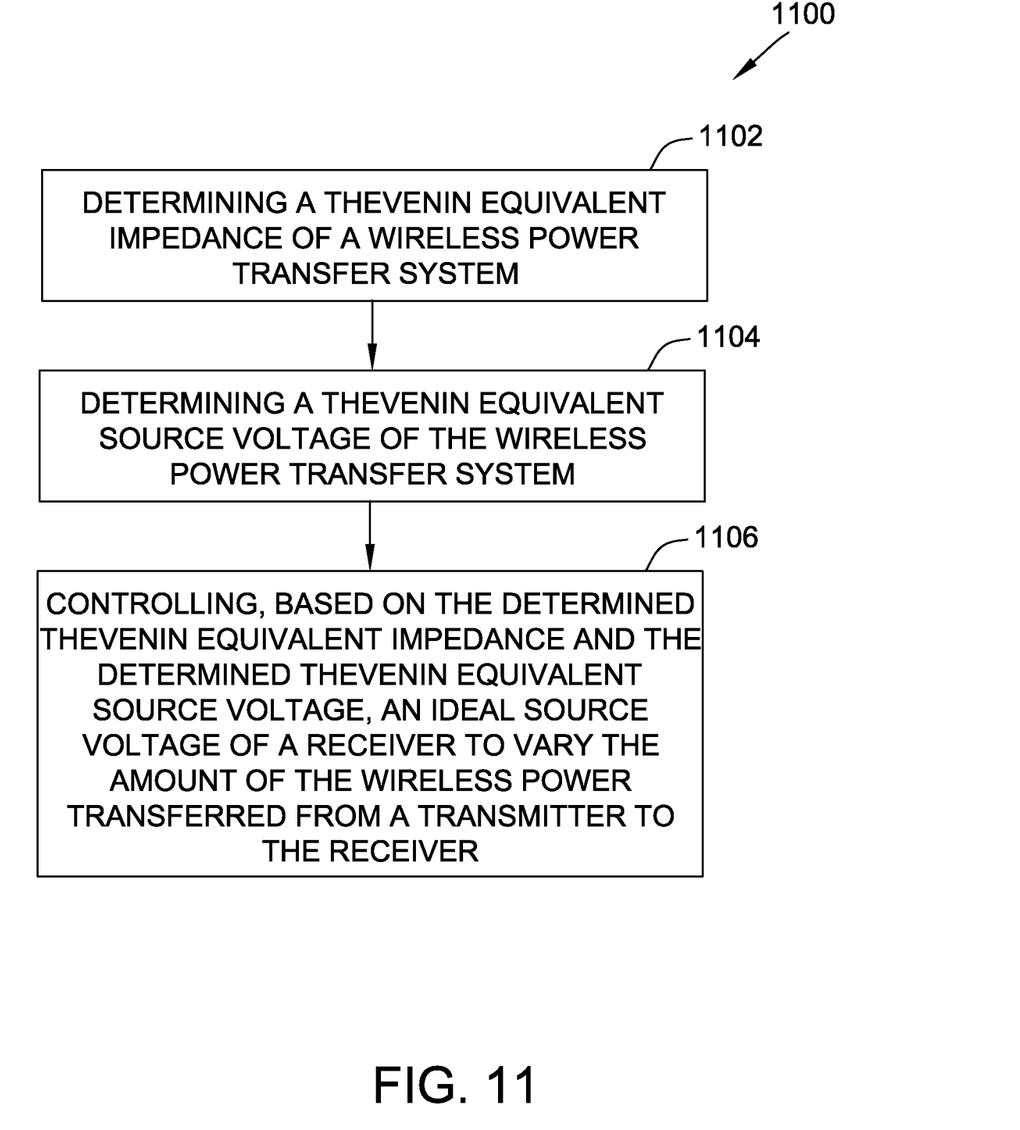
FIG. 11 is a flow chart of one embodiment of a method for controlling operation of a wireless power transfer system.

FIG. 11 is a flow chart of one embodiment of a method 1100 for controlling a wireless power transfer system. Method 1100 may be implemented, for example, using computing device 1000 (shown in FIG. 10). In this embodiment, method 1100 includes determining 1102 a Thevenin equivalent impedance of the wireless power transfer system. Method 1100 further includes determining 1104 a Thevenin equivalent source voltage of the wireless power transfer system. Method 1100 further includes controlling 1106, based on the determined Thevenin equivalent impedance and the determined Thevenin equivalent source voltage, an ideal source voltage of the receiver to vary the amount of the wireless power transferred from the transmitter to the receiver.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims. Although described in some respects as a medical system, one will appreciate from the description herein that the principles can apply equally to other types of systems including, but not limited to, consumer electronics, automotive, phones and personal communication devices, gaming devices, and computers and peripherals.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wireless power transfer system comprising:
 a transmitter driven by a power source and a transmit controller, wherein the transmitter is configured to control delivery of wireless power; and
 a receiver inductively coupled to the transmitter, the receiver configured to receive the wireless power from the transmitter and deliver the received wireless power to a load as direct current (DC) power via a converter circuit, the receiver comprising a control system configured to:
  calculate a Thevenin equivalent impedance of the wireless power transfer system from the point of view of the receiver based on current measurements at an input of the converter circuit;
  calculate a maximum allowed voltage using a cutback function that monitors the Thevenin equivalent impedance and calculates the maximum allowed voltage based on the Thevenin equivalent impedance; and
  control, using a controller, the converter circuit to control an ideal source voltage at the input of the converter circuit based on the calculated Thevenin equivalent impedance to vary an amount of the wireless power transferred from the transmitter to the receiver, wherein an output of the controller is limited to the maximum allowed voltage.

2. The wireless power transfer system of claim 1, wherein to control the converter circuit to control the ideal source voltage, the control system is configured to increase the ideal source voltage to increase a DC current associated with the DC power.

3. The wireless power transfer system of claim 1, wherein the converter circuit is a MOSFET bridge, and wherein to control the converter circuit to control the ideal source voltage, the control system is configured control the MOSFET bridge to drive the ideal source voltage.

4. The wireless power transfer system of claim 3, wherein the control system is configured to control the MOSFET bridge by controlling a duty cycle and a phase of a pulse width modulated signal that drives the MOSFET bridge.

5. The wireless power transfer system of claim 1, wherein the control system is configured to control the converter circuit to control the ideal source voltage to be in phase with an ideal source current of the receiver at the input of the converter circuit.

6. The wireless power transfer system of claim 1, wherein the controller is a proportional integrative (PI) controller.

7. A receiver for use in a wireless power transfer system, the receiver configured to receive wireless power from a transmitter driven by a power source and a transmit controller, and configured to deliver the received wireless power to a load as direct current (DC) power via a converter circuit, the receiver comprising:

a receiving coil; and a control system coupled to the receiving coil, the control system configured to:

calculate a Thevenin equivalent impedance of the wireless power transfer system from the point of view of the receiver based on current measurements at an input of the converter circuit;

calculate a maximum allowed voltage using a cutback function that monitors the Thevenin equivalent impedance and calculates the maximum allowed voltage based on the Thevenin equivalent impedance; and control, using a controller, the converter circuit to control an ideal source voltage at the input of the converter circuit based on the calculated Thevenin equivalent impedance to vary an amount of the wireless power transferred from the transmitter to the receiver, wherein an output of the controller is limited to the maximum allowed voltage.

8. The receiver of claim 7, wherein to control the converter circuit to control the ideal source voltage, the control system is configured to increase the ideal source voltage to increase a DC current associated with the DC power.

9. The receiver of claim 7, wherein the converter circuit is a MOSFET bridge, and wherein to control the converter circuit to control the ideal source voltage, the control system is configured control the MOSFET bridge to drive the ideal source voltage.

10. The receiver of claim 9, wherein the control system is configured to control the MOSFET bridge by controlling a duty cycle and a phase of a pulse width modulated signal that drives the MOSFET bridge.

11. The receiver of claim 7, wherein control system is configured to control the converter circuit to control the ideal source voltage to be in phase with an ideal source current of the receiver.

12. The receiver of claim 7, wherein the controller is a proportional integrative (PI) controller.

13. A method for controlling a wireless power transfer system, the wireless power transfer system including a receiver inductively coupled to a transmitter, the receiver configured to receive wireless power from the transmitter and deliver the received wireless power to a load as direct current (DC) power via a converter circuit, the method comprising:

calculating, using a control system, a Thevenin equivalent impedance of the wireless power transfer system from the point of view of the receiver based on current measurements at an input of the converter circuit;

calculating a maximum allowed voltage using a cutback function that monitors the Thevenin equivalent impedance and calculates the maximum allowed voltage based on the Thevenin equivalent impedance; and controlling, using a controller of the control system, the converter circuit to control an ideal source voltage at the input of the converter circuit based on the calculated Thevenin equivalent impedance to vary an amount of the wireless power transferred from the transmitter to the receiver, wherein an output of the controller is limited to the maximum allowed voltage.

14. The method of claim 13, wherein controlling the converter circuit further comprises increasing the ideal source voltage to increase a DC current associated with the DC power.

15. The method of claim 13, wherein the converter circuit is a MOSFET bridge, and wherein controlling the converter circuit to control the ideal source voltage comprises controlling the MOSFET bridge to drive the ideal source voltage.

16. The method of claim 15, wherein controlling the MOSFET bridge comprises controlling a duty cycle and a phase of a pulse width modulated signal that drives the MOSFET bridge.

17. The method of claim 13, wherein controlling the convert circuit further comprises controlling the converter circuit to control the ideal source voltage to be in phase with an ideal source current of the receiver at the input of the converter circuit.

18. The method of claim 13, wherein controlling the convert circuit further comprises controlling, using a proportional integrative (PI) controller of the control system, the converter circuit to control the ideal source at the input of the converter circuit, wherein an output of the PI controller is limited to the maximum allowed voltage.

\* \* \* \* \*